US011116863B2

(12) United States Patent
Kim et al.

(10) Patent No.: US 11,116,863 B2
(45) Date of Patent: Sep. 14, 2021

(54) AIR CLEANER

(71) Applicant: Seoul Viosys Co., Ltd., Ansan-si (KR)

(72) Inventors: Jong Rack Kim, Ansan-si (KR); Jae Hak Jeong, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 363 days.

(21) Appl. No.: 16/094,782

(22) PCT Filed: Mar. 29, 2017

(86) PCT No.: PCT/KR2017/003384
§ 371 (c)(1),
(2) Date: Oct. 18, 2018

(87) PCT Pub. No.: WO2017/183824
PCT Pub. Date: Oct. 26, 2017

(65) Prior Publication Data
US 2019/0125917 A1   May 2, 2019

(30) Foreign Application Priority Data
Apr. 18, 2016  (KR) .................. 10-2016-0047138

(51) Int. Cl.
*A61L 9/16* (2006.01)
*A61L 9/20* (2006.01)
(Continued)

(52) U.S. Cl.
CPC .............. *A61L 9/205* (2013.01); *A61L 9/20* (2013.01); *B01D 46/0005* (2013.01);
(Continued)

(58) Field of Classification Search
None
See application file for complete search history.

(56) References Cited

U.S. PATENT DOCUMENTS

| 4,380,007 A | 4/1983 | Steinegger |
| 5,078,971 A * | 1/1992 | Matuda ............... A61L 9/16 |
| | | 261/DIG. 88 |

(Continued)

FOREIGN PATENT DOCUMENTS

| CN | 204611988 | 9/2015 |
| JP | S60-010648 | 1/1985 |

(Continued)

OTHER PUBLICATIONS

Machine translation for JP 61-249555 A. Retrieved from JPO website on Dec. 10, 2020. (Year: 2020).*

(Continued)

*Primary Examiner* — Jennifer A Leung
(74) *Attorney, Agent, or Firm* — H.C. Park & Associates, PLC

(57) ABSTRACT

An air cleaner includes: a body formed with an air suction hole defined on a side of the body, and allowing air to be introduced into the body therethrough; a metal casing into which an upper section of the body is inserted from below; a flow creation mechanism disposed inside the casing to create an air flow into and through the air cleaner; a filter disposed in the body between the air suction hole and the flow creation mechanism configured to purify air; a capacitive switch partially exposed outside the casing through a switch exposure hole defined through the casing; and a printed circuit board (PCB) disposed between one side wall of the upper section of the body and an inner wall of the casing.

18 Claims, 6 Drawing Sheets

(51) Int. Cl.
*B01D 46/10* (2006.01)
*B01D 46/42* (2006.01)
*B01D 53/88* (2006.01)
*B01D 46/00* (2006.01)
*B01D 46/44* (2006.01)
*B01D 53/00* (2006.01)

(52) U.S. Cl.
CPC ......... *B01D 46/0038* (2013.01); *B01D 46/44* (2013.01); *B01D 53/007* (2013.01); *B01D 53/885* (2013.01); *A61L 2209/12* (2013.01); *A61L 2209/14* (2013.01); *B01D 46/10* (2013.01); *B01D 2255/20707* (2013.01); *B01D 2255/20715* (2013.01); *B01D 2255/20776* (2013.01); *B01D 2255/20792* (2013.01); *B01D 2255/802* (2013.01); *B01D 2257/708* (2013.01); *B01D 2258/06* (2013.01); *B01D 2259/4508* (2013.01); *B01D 2259/804* (2013.01); *B01D 2273/30* (2013.01); *B01D 2279/50* (2013.01); *B01D 2279/65* (2013.01)

(56) References Cited

U.S. PATENT DOCUMENTS

| | | | | |
|---|---|---|---|---|
| 6,000,559 | A * | 12/1999 | Stopyra | H05K 7/1417 211/41.17 |
| 8,203,091 | B2 * | 6/2012 | Kang | F24F 1/0007 200/314 |
| 2006/0201119 | A1 | 9/2006 | Song | |
| 2008/0019861 | A1 * | 1/2008 | Silderhuis | A61L 9/20 422/3 |
| 2010/0095844 | A1 * | 4/2010 | Gilleland | B01D 46/0036 95/148 |
| 2011/0100221 | A1 * | 5/2011 | Wu | F24F 1/0071 96/16 |
| 2015/0064069 | A1 * | 3/2015 | Yi | B01D 46/0028 422/121 |
| 2016/0256590 | A1 * | 9/2016 | Taghipour | A61L 9/205 |
| 2020/0061231 | A1 * | 2/2020 | Jeong | B01D 46/0009 |

FOREIGN PATENT DOCUMENTS

| | | | |
|---|---|---|---|
| JP | 61249555 | A * | 11/1986 |
| JP | H11-216336 | | 8/1999 |
| JP | 2012-134148 | | 7/2012 |
| JP | 2016-050687 | | 4/2016 |
| KR | 10-0508312 | | 8/2005 |
| KR | 10-2010-0058742 | | 6/2010 |
| KR | 10-2011-0059225 | | 6/2011 |
| KR | 10-2016-0015084 | | 2/2016 |

OTHER PUBLICATIONS

International Search Report dated Jun. 30, 2017 in International Application No. PCT/KR2017/003384 (with English Translation).
Written Opinion dated Jun. 30, 2017 in International Application No. PCT/KR2017/003384 (with English Translation).
Notice of Reasons for Refusal dated Feb. 9, 2021 issued in Japanese Patent Application No. 2018-554739.
Office Action dated Oct. 9, 2020 for Chinese Patent Application No. 201780024472.2.
Shoujiang Liu, Principle and Maintenance of Air Conditioner and Microcomputer Controller Thereof.

* cited by examiner

AIR CLEANER

CROSS REFERENCE TO RELATED APPLICATIONS

This application is the National Stage Entry of International Patent Application No. PCT/KR2017/003384, filed on Mar. 29, 2017, and claims priority from and the benefit of Korean Patent Application No. 10-2016-0047138, filed on Apr. 18, 2016, each of which is incorporated by reference for all purposes as if fully set forth herein.

BACKGROUND

Field

Exemplary embodiments/implementations of the invention relate generally to an air cleaner and, more particularly, to a small air cleaner.

Discussion of the Background

Generally, an air cleaner uses a blower such as a fan to circulate air through various filters such as a prefilter, a deodorizing filter, and a HEPA filter to remove pollutants including fine dust, bacteria, and volatile organic compounds (VOCs) such as formaldehyde from the air.

Recently, as it has been known that air pollutants can be released from furniture, office supplies, home appliances, interior paints on new houses, interior goods, automobile interior materials, toilets, and the like, there is a growing interest in indoor air quality. Accordingly, there is increasing demand for a small air cleaner, which is easy to install and simple to use and does not take up much space and is thus suitable for use in houses, offices, automobiles, and the like.

Recently, the development of semiconductor technology has enabled high-efficiency UV light emitting diodes to be produced at lower costs. As a result, photocatalytic filters are widely used as deodorizing filters. A photocatalytic filter is fabricated by coating an air-permeable material, such as metal foam or porous metal, with a photocatalytic material such as $TiO_2$, $ZnO$, $ZrO_2$, or $WO_3$, and can generate hydroxyl radicals to decompose contaminants or odorous substances when irradiated with UV light. Such a photocatalytic filter can be reused through cleaning after a certain period of use.

However, in the case of typical small air cleaners, it is difficult to disassemble a case in order to take a reusable filter such as a deodorizing filter or a prefilter out of the air cleaner. Therefore, there is a need for an air cleaner which allows easy replacement and attachment/detachment of a filter.

In addition, since a typical small air cleaner is small enough to be installed in a narrow place such as on a desk and has an air flow passage therein, internal components thereof, such as a printed circuit board (PCB), need to have small sizes and switches thereof, such as a power switch, need to be operable with a light touch. That is, operating a push switch, a seesaw switch, or a trigger switch can cause an air cleaner to move or fall.

The above information disclosed in this Background section is only for understanding of the background of the inventive concepts, and, therefore, it may contain information that does not constitute prior art.

SUMMARY

Exemplary embodiments of the inventive concepts have been conceived to provide an air cleaner which is easy to disassemble, thereby allowing easy replacement and attachment/detachment of a filter.

It is another aspect of the present disclosure to provide an air cleaner having a switch operable with a light touch.

It is a further aspect of the present disclosure to provide an air cleaner having a structure that can facilitate product assembly while reducing occurrence of defects.

Additional features of the inventive concepts will be set forth in the description which follows, and in part will be apparent from the description, or may be learned by practice of the inventive concepts.

Exemplary embodiments of an air cleaner include: a body formed with a plurality of air suction holes defined on a side of the body, and allowing air to be introduced into the body therethrough; a metal casing, an upper section of the body is inserted into the metal casing from below; a flow creation mechanism disposed inside the casing to create an air flow into and through the air cleaner; a filter disposed in the body between the air suction hole and the flow creation mechanism configured to purify air; a capacitive switch partially exposed outside the casing through a switch exposure hole defined through the casing; and a printed circuit board (PCB) disposed between one side wall of the upper section of the body and an inner wall of the casing.

The capacitive switch may include a touch button exposed through the switch exposure hole and a conductive gasket disposed between the touch button and the PCB to electrically connect the touch button to the PCB.

The conductive gasket may include a cuboidal elastic foam member and a conductive tape wrapped around the cuboidal elastic foam member.

A surface of the touch button contacting the conductive gasket may be curved inward.

The touch button may have a larger width than the conductive gasket.

A wall portion of the casing defining the switch exposure hole may be rounded on an inner side thereof.

The air cleaner may further include a support fin protruding from the one side wall of the body and includes a free end extending to contact an inner surface of the casing.

The body may include a thickened portion formed at a lower end of the upper section of the body.

The body may include a secured portion connected to the upper section, and an upper surface of the secured portion connected to the upper section extends from both side edges of the upper surface beyond the upper section to form a stepped portion.

With the upper section inserted into the casing, a lower end of the casing may contact the stepped portion.

The body may include a secured portion connected to the upper section, the secured portion may include a rail member formed inside the secured portion.

The air cleaner may further include a guide portion formed on an upper side of the rail member to receive the filter.

The air cleaner may further include a UV module disposed above the filter configured to emit UV light toward the filter.

The filter may be a photocatalytic filter.

The air cleaner may further include a cover detachably coupled to the secured portion.

The cover may include a guide bar, the guide bar being fastened to the rail member to couple the cover to the secured portion.

The air cleaner may further include a light shielding member disposed inside the body adjacent to a junction between an upper end of the cover and a lower end of the casing.

In accordance with a first aspect of the present disclosure, an air cleaner includes: a body formed with an air suction hole allowing air to be introduced into the body therethrough; a casing receiving an upper section of the body; a fan mounted in the casing to generate a flow of air; and a filter disposed in the body downstream of the air suction hole, wherein the body comprises a cover detachably coupled to a lower section of the body.

In accordance with a second aspect of the present disclosure, an air cleaner includes: a body formed with an air suction hole allowing air to be introduced into the body therethrough; a casing receiving an upper section of the body; a fan mounted in the casing to generate a flow of air; a filter disposed in the body downstream of the air suction hole; and a capacitive switch disposed on one side of the casing.

The air cleaner according to the second aspect may further include a support fin protruding from an inserted part of the body inserted into the casing.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
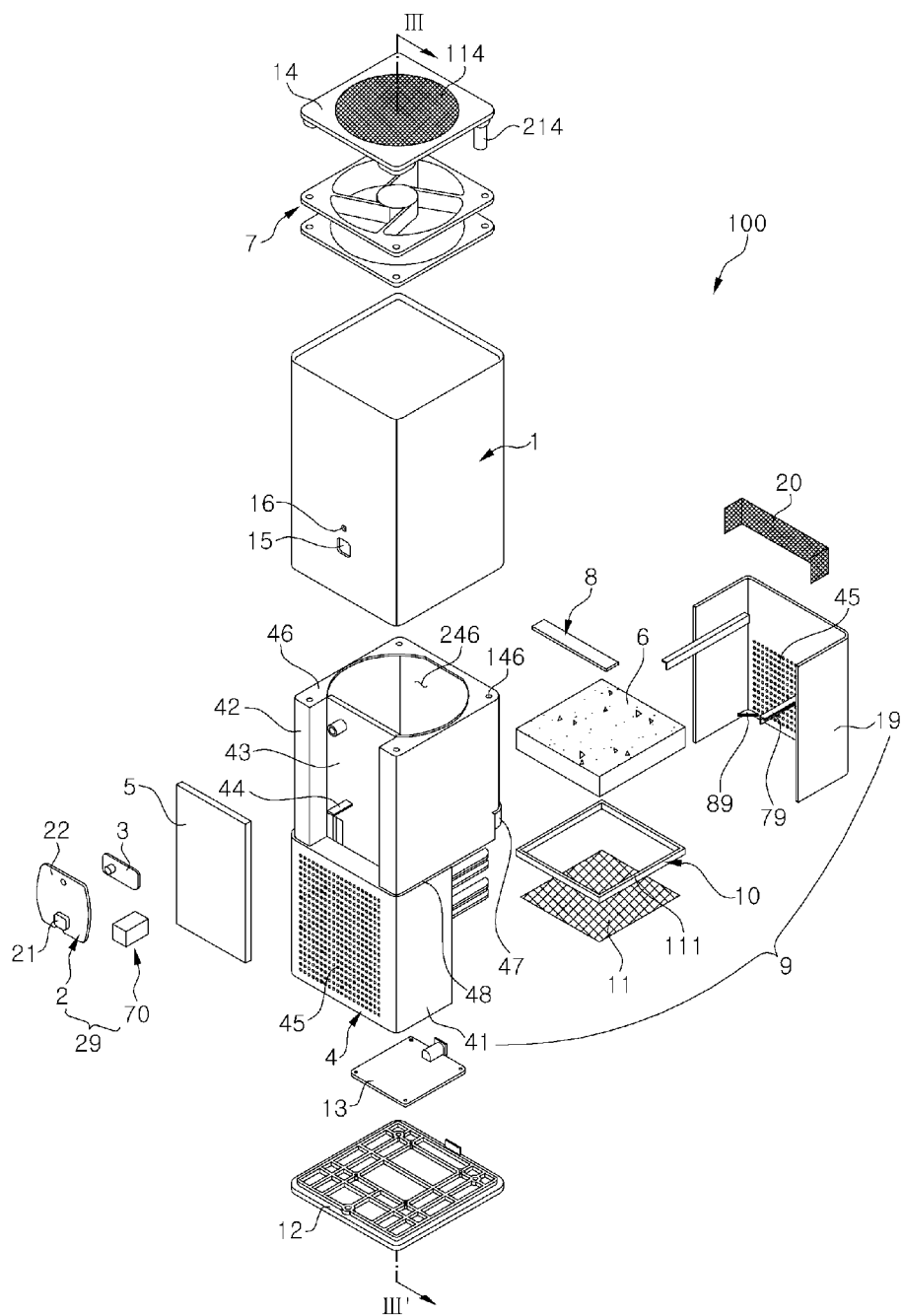
FIG. 1 is a front exploded perspective view of an air cleaner according to one exemplary embodiment of the present disclosure.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z—axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
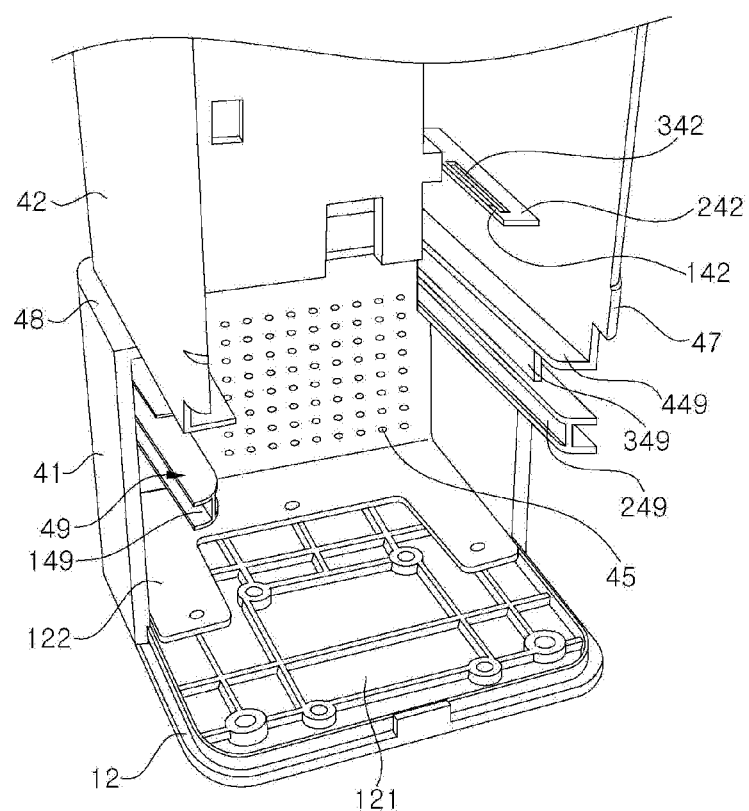
FIG. 2 is a schematic rear perspective view of a body of the air cleaner according to the exemplary embodiment.
Figure 3:
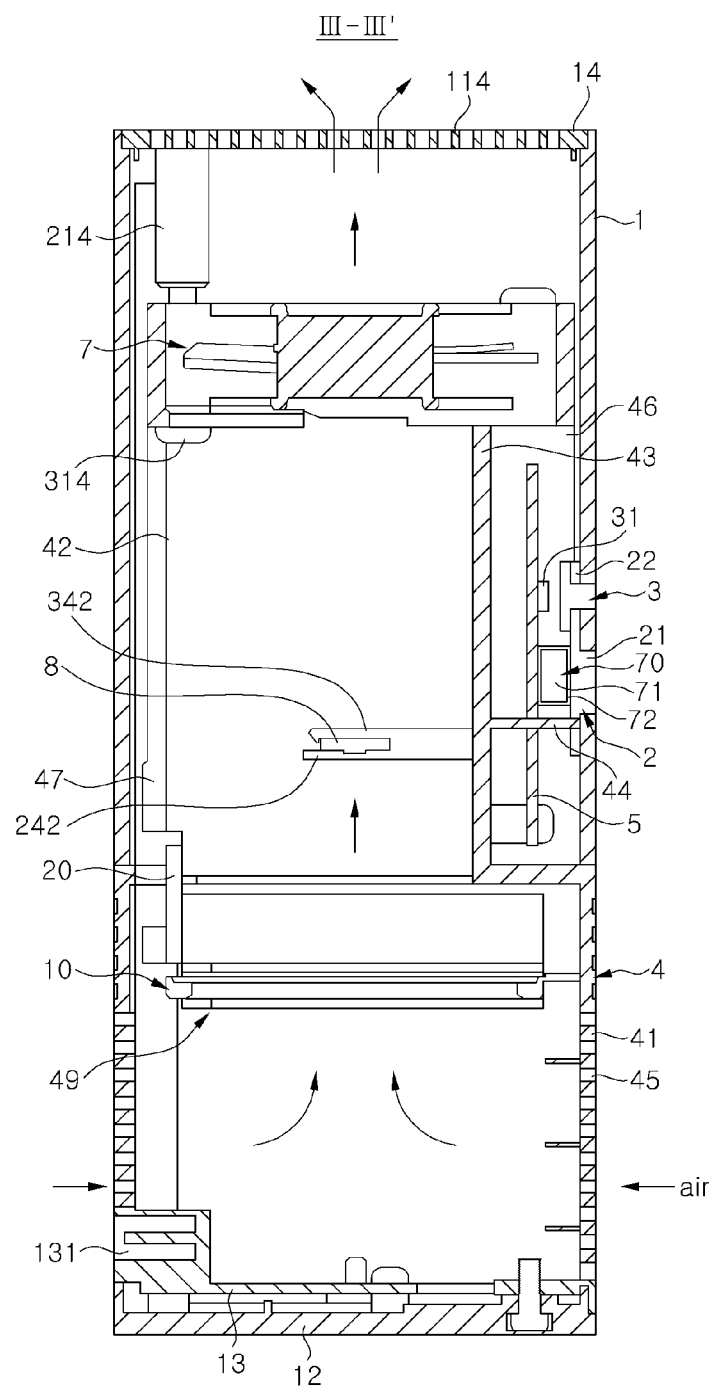
FIG. 3 is a schematic cross-sectional view taken along line of FIG. 1.

FIG. 1 is a front exploded perspective view of an air cleaner according to one exemplary embodiment of the present disclosure, FIG. 2 is a rear perspective view of a body of the air cleaner according to the exemplary embodiment, and FIG. 3 is a schematic cross-sectional view taken along line of FIG. 1.

Referring to FIG. 1, an air cleaner 100 according to an exemplary embodiment includes a body 4 formed with an air suction hole 45, a casing 1 receiving an upper section of the body 4, a fan 7 disposed inside the casing 1 to create an air flow into and through the casing 1, a UV module 8, a filter 6, and prefilter 10 disposed in the body 4 below the air suction hole 45 to allow the air flow to pass therethrough. A flow creation mechanism may include, but is not limited to, the fan 7 and an opening 246, and other related parts that could create an air flow.

The body 4 may be formed of a resin such as an acrylonitrile-butadiene-styrene (ABS) resin and may have a substantially quadrangular prism shape, as shown in the drawings. However, it should be understood that the present disclosure is not limited thereto and the body may have, for example, a cylindrical shape or a truncated cone shape.

The body 4 includes an exposed part 9 at a lower section thereof and an inserted part 42 at the upper section thereof, wherein the inserted part 42 is configured to be inserted into the casing 1. The body includes a stepped portion 48 formed at a portion of the exposed part 9 connected to the inserted part 42, wherein the stepped portion tightly contacts a lower end of the casing 1 when the inserted part 42 of the body 4 is inserted into the casing 1.

The exposed part 9 includes a secured portion 41 securely connected to the inserted part 42 and detachably connected to a cover 19. Referring to FIG. 1, an air suction hole 45 allowing air to flow into the air cleaner 100 therethrough may be formed through each of a front side of the secured portion 41 and a rear side of the cover 19. However, it should be understood that the position and shape of the air suction hole 45 are not limited thereto and the air suction hole 45 may also be formed through other sides of the exposed part 9.

Referring to FIG. 2, the secured portion 41 may be provided t outside of a rail member 49 on which a prefilter 10 is mounted. The rail member 49 may have an I-shaped cross section and may include a pair of rail members disposed on respective opposite inner sides of the secured portion 41. The pair of rail members 49 may include respective inner rails 249 facing one another and respective outer rails 149 facing outward. A frame 111 supporting a mesh 11 of the prefilter 10 may be detachably fitted into the inner rails 249. In addition, when the cover 19 is mounted on the secured portion 41, guide bars 79 of the cover 19 may be detachably fitted into the respective outer rails 149 to assist in accurate alignment of the cover 19 and to prevent movement of the cover 19 during a subsequent screw fastening process as described below, thereby enabling smooth screw fastening.

In addition, a pair of guide portions 349 facing one another may be formed on respective upper sides of the pair of rail members 49 inside the secured portion 41, such that a photocatalytic filter 6 can be detachably inserted between the upper side of the rail member 49 and the guide portion 349. A UV module 8 may be disposed above the photocatalytic filter 6 to emit UV light toward the photocatalytic filter 6 to activate the photocatalytic filter 6. The UV module 8 includes a circuit board and a light emitting device attached to a lower surface of the circuit board. The light emitting device may emit UV light at a wavelength of, for example, 388 nm or less, preferably, 365 nm or less so as to improve photocatalytic efficiency.

The cover 19 of the exposed part 9 may be detachably connected to the secured portion 41. When the cover is mounted on the secured portion, the guide bars 79 of the cover 19 may be inserted into the respective outer rails 149 of the pair of rail members 49, as described above. In addition, the cover 19 may be provided at opposite lower corners thereof with a pair of corner flanges 89.

A bottom cover 12 may be coupled to a lower end of the body 4 using fastening members, such as screws, driven from a lower surface of the bottom cover 12 (see FIG. 3). Here, some screws may be connected to a mounting flange 122 of the secured portion 41 and the other screws may be connected to the corner flanges 89 of the cover 19 to prevent the cover 19 from being separated from the secured portion 41. A power PCB 13 may be secured to an upper surface of the bottom cover 12. In addition, the power PCB 13 may be connected to a connector 131 for connection with an external power supply, as shown in FIG. 3, wherein the cover 19 may be formed with a cutout or a through-hole for exposing the connector 131.

Further, the body 4 may include a horizontal inner wall portion 449 formed at a portion of the inserted part 42 connected to the secured portion 41 and having a predetermined width to guide the photocatalytic filter 6 from above, as shown in FIG. 2.

The inserted part 42 of the body 4 is configured to be inserted into the casing 1 and may include a recessed PCB mount 43 formed on one side thereof, for example, a front side thereof, to receive a PCB 5 for power distribution of the air cleaner 100, as shown in FIG. 1. The PCB 5 may be secured to the PCB mount 43 by driving a screw into a screw-receiving portion provided to the PCB mount 43. The PCB 5 is secured to the PCB mount 43 to be spaced a predetermined distance away from the casing 1, as shown in FIG. 3. In the space between the PCB 5 and the casing, a conductive gasket 70 described below is disposed to electrically connect the PCB 5 to a switch actuator 2 which may be attached to an inner surface of the casing 1, wherein the conductive gasket 70 and the switch actuator 2 constitute a capacitive switch 29.

In addition, the PCB mount 43 is provided with a support fin 44 which has a free end configured to tightly contact the inner surface of the casing 1, as shown in FIG. 3. As shown in the drawings, the support fin 44 may be provided in the form of a thin plate protruding through a through-hole of the PCB 5, having a predetermined width in a horizontal direction, and being capable of generating elastic force. The support fin 44 may be disposed under the conductive gasket 70 to suppress a free end of the conductive gasket 70 attached to the PCB 5 from being pushed downward by the inner wall of the casing 1 when the inserted part 42 is inserted into the casing 1 during assembly of the air cleaner 100, thereby enabling smooth assembly of the air cleaner 100. In addition, with the inserted part 42 inserted into the casing, the free end of the support fin 44 is pressed against the inner surface of the casing 1, thereby allowing accurate and reliable alignment of the casing 1 with the body 4 in cooperation with the stepped portion 48 and a thickened portion 47 described below.

Although the support fin 44 is shown as flat in this exemplary embodiment, it should be understood that the present disclosure is not limited thereto and the support fin may have any suitable shape, so long as the shape of the support fin can prevent the conductive gasket 70 from being pushed downward when the inserted part 42 is inserted into the casing 1.

In addition, the PCB mount 43 may be formed with a through-hole through which a wire for electrical connection with the power PCB 13, the UV module 8 and the like passes.

An upper side 46 of the inserted part 42 is formed with an opening 246 allowing an air flow to pass therethrough. Further, the upper side 46 of the inserted part 42 is provided at a corner thereof with an insertion protrusion 146 configured to be fitted into a corresponding recess formed at the corner of a lower side of the fan 7, thereby facilitating and retaining alignment of the fan 7 with the upper side 46, whereby a process of securing the fan 7 to the upper side 46 of the inserted part 42 using a fastening member such as a screw can be easily performed, as shown in FIG. 3.

The inserted part 42 may include a pair of support wall portions 242 and a pair of catching pieces 342 formed on respective opposite inner side walls thereof to allow the UV module 8 to be mounted thereon, as shown in FIG. 2. With the circuit board of the UV module 8 inserted between the support wall portion 242 and the catching piece 342, the UV module 8 is located above the center of the photocatalytic filter 6, as shown in FIG. 3, whereby UV light can be evenly radiated throughout the photocatalytic filter 6. An inner surface of the inserted part 42 may be coated with a reflective film (not shown) to increase reflectance of light that is emitted from the UV module 8 and has a wavelength of, for example, 388 nm or less, preferably 365 nm or less to improve photocatalytic efficiency.

In addition, the inserted part 42 may include a thickened portion 47 formed at a rear lower end thereof. As shown in FIG. 2, the thickened portion 47 may extend a predetermined length in a vertical direction and protrude slightly further outward or sideways than the rest of the inserted part 42. Accordingly, with the inserted part mounted in the casing, the rest of the inserted part 42 can be spaced apart from the inner surface of the casing 1, whereas the thickened portion 47 can be firmly held against the inner surface of the casing to improve and retain accuracy and reliability of alignment of the body with the casing 1, thereby improving integrity of the assembled air cleaner 100 in cooperation with the support fin 44 extending forwardly of the inserted part 42.

The casing 1 receiving the inserted part 42 may be formed of, for example, aluminum and may have a quadrangular prism shape corresponding to the body 4, as shown in FIG. 1, without being limited thereto. The casing 1 is open at the top and bottom thereof and may have a stepped upper end allowing an exhaust cover 14 to be attached thereby when the exhaust cover 14 is mounted into the casing 1, as shown in FIG. 3.

The inner size of the casing 1 is slightly larger than the outer size of the inserted part 42, such that, with the inserted part mounted in the casing, a small gap, for example, a gap having a size of 0.2 mm to 0.4 mm can be formed between the inner surface of the casing 1 and the inserted part 42. However, the casing 1 can be firmly connected to the inserted part 42 by the cooperation of the support fin 44, the thickened portion 47, and the stepped portion 48, as described above.

The casing 1 may include a switch exposure hole 15 formed through a front wall thereof to expose a touch button 21 of the switch actuator 2 constituting the capacitive switch 29. The casing may further include a mounting hole 16 formed above the switch exposure hole 15 to allow a light transmissive member 3 to be inserted thereinto. The light transmissive member 3 transmits or scatters light from a light emitting device 31 provided to the PCB 5, thereby displaying the operating status of the air cleaner 100, such as an On/Off status.

Figure 4:
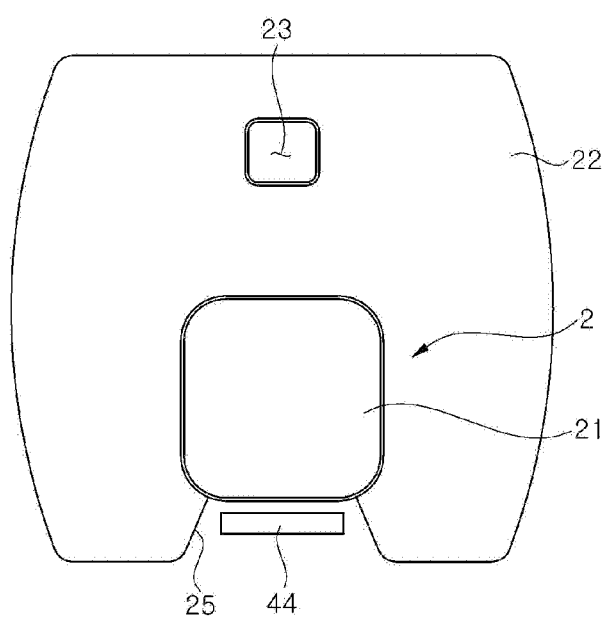
FIG. 4 is a schematic plan view of a switch actuator of the air cleaner according to the exemplary embodiment.

The switch actuator 2 includes the touch button 21 which is exposed outside the casing 1 through the switch exposure hole 15 to be touched by a user's finger or the like, as shown in FIG. 4. In addition, the switch actuator 2 may include a flat attachment portion 22 which horizontally extends around the touch button 21 to be attached to the inner surface of the casing 1, as shown in FIG. 4. In addition, the attachment portion 22 may be formed with a mounting hole 23 into which the light transmissive member 3 is fitted.

Further, the attachment portion 22 may be formed with a cutout 25 allowing the support fin 44 to be disposed adjacent to the touch button 21.

The touch button 21 serves to transmit electrostatic charge of the human body to the conductive gasket 70 when touched by the human body and may be formed of, for example, acryl, glass or rubber. Upon receiving the electrostatic charge from the touch button 21, the conductive gasket 70 generates a touch signal. A portion of the conductive gasket 70 opposite a portion contacting the touch button 21 may be attached and connected to the PCB 5.

Figure 5:
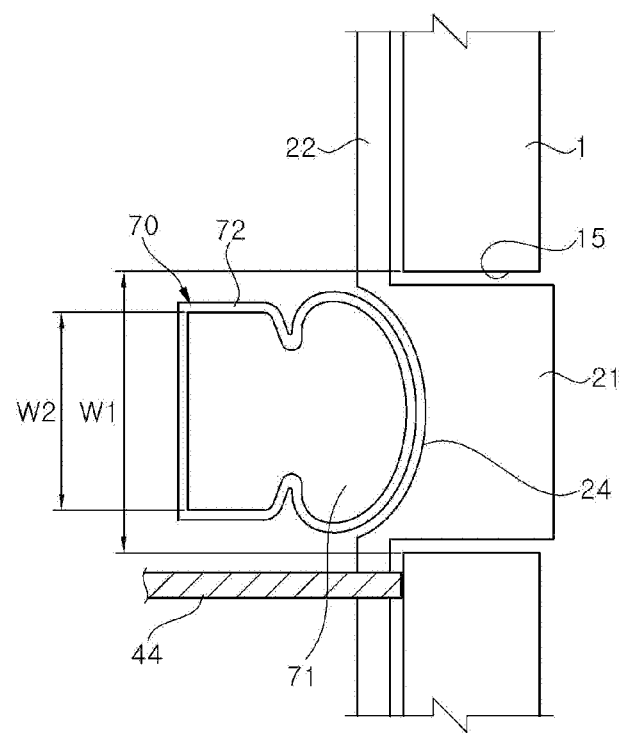
FIG. 5 is a schematic partial cross-sectional view of a capacitive switch section of the air cleaner according to one exemplary embodiment of the present disclosure.
Figure 6:
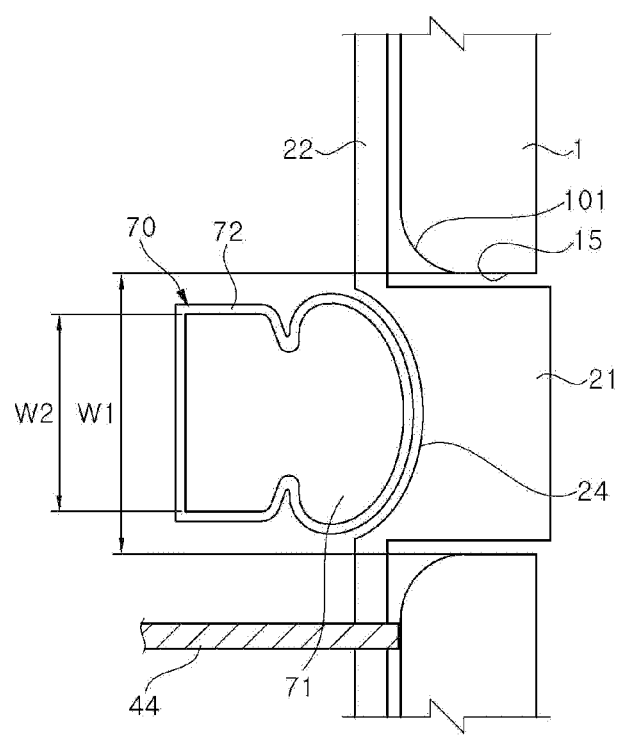
FIG. 6 is a schematic partial cross-sectional view of a capacitive switch section of the air cleaner according to another exemplary embodiment of the present disclosure.

Now, the touch button 21 and the conductive gasket 70 will be described in more detail with reference to FIG. 5. Referring to FIG. 5, an upper surface of the touch button 21 exposed through the switch exposure hole 15 of the casing 1 may be substantially flush with the outer surface of the casing 1. A contact surface 24 of the touch button 21 opposite the exposed upper surface tightly contacts the conductive gasket 70. The contact surface 24 may be formed flat or may be curved inward to increase a contact area with respect to the conductive gasket. In the latter case, a surface of the conductive gasket 70 contacting the touch button 21 may be curved outward to correspond in shape to the inwardly curved contact surface 24. In this way, the contact area between the touch button 21 and the conductive gasket 70 can be increased, thereby allowing smoother transmission of the electrostatic charge.

In addition, the conductive gasket 70 may include a cuboidal elastic foam member 71, such as urethane or sponge foam, and a conductive tape 72 wrapped around the foam member 71. However, it should be understood that the present disclosure is not limited thereto and the conductive gasket 70 may be configured in any suitable way and may be formed of any suitable material. In addition, as shown in FIG. 3 or FIG. 5, the conductive tape 72 may be wrapped around the foam member 71 only in vertical cross-section.

With the body mounted in the casing, the conductive gasket 70 is slightly compressed against the contact surface 24 and a side of the conductive gasket 70 opposite the side of the conductive gasket tightly contacting the contact surface 24 may be securely attached to an electrode of the PCB 5 via, for example, a conductive adhesive.

Referring to FIG. 5, the width W2 of the conductive gasket 70 is smaller than the width W1 of the switch exposure hole 15 to improve operational stability and accuracy of the capacitive switch 29. That is, even when the casing 1 is formed of a metal such as aluminum, the capacitive switch 29 can be operated stably and accurately.

In order to further improve operational stability and accuracy of the capacitive switch 29, a wall portion of the casing 1 defining the switch exposure hole 15 may include a rounded portion 101 facing inwardly of the casing 1.

The exhaust cover 14 disposed at the upper end of the casing 1 includes an air outlet 114 through which air is discharged from the air cleaner 100 by the fan 7. The exhaust cover 14 may include a pair of screw receiving portions 214 which extends from two corners (rear corners in FIG. 1) of the lower surface of the exhaust cover, respectively. The exhaust cover 14 may be secured to the upper end of the casing 1 by connecting the fan to the insertion protrusions 146 on the upper side 46 of the body 4, securing the fan to two front corners of the upper side of the body using screws driven from above the fan 7, and driving screws 314 into the screw receiving portions 214 from below the upper side 46 of the inserted part 42.

A light shielding member 20 may be disposed inside the lower end of the casing 1, as shown in FIG. 3. The light shielding member 20 serves to prevent light from the UV module 8 from leaking through a possible gap between the casing and the cover 19 and may be formed of an opaque film or the like. The light shielding member 20 may be disposed behind the photocatalytic filter 6 to cover a junction between the lower end of the casing 1 and the upper end of the cover 19.

Next, a process of replacing filters of the air cleaner 100 set forth above will be described.

First, the screws driven into the corner flanges 89 of the cover 19 from the lower surface of the bottom cover 12 are released and then the cover 19 is pulled backward to be removed from the secured portion 41.

Then, the prefilter 10 and the photocatalytic filter 6 are drawn out of the rail member 49 and the photocatalytic filter guide portion 349, respectively, to be withdrawn from the body 4. The withdrawn prefilter 10 and filter 6 may be cleaned with water or the like, followed by drying, and then may be mounted back on the rail member 49 and the photocatalytic filter guide portion 349 of the body 4, respectively.

After the filters are remounted, the cover 19 may be secured to the secured portion 41 in reverse order of removal.

As described above, the air cleaner according to the present disclosure is easy to disassemble, thereby allowing easy removal/mounting of the filters. In addition, with the capacitive switch, operations such as power On/Off can be performed without changing the position of the air cleaner. Further, with the support fin disposed on the PCB mount, it is possible to prevent the conductive gasket, which constitutes the capacitive switch, from being pushed away by the casing during assembly of the air cleaner, thereby improving product quality and productivity. Other advantages of the present disclosure will also be readily appreciated by those skilled in the art.

Although some exemplary embodiments have been described herein, it should be understood that these exemplary embodiments are provided for illustration only and are not to be construed in any way as limiting the present disclosure, and that various modifications, changes, alterations, and equivalent exemplary embodiments can be made by those skilled in the art without departing from the spirit and scope of the disclosure. For example, although it has been described that the air outlet is provided to the exhaust cover, additionally or alternatively, the air outlet may be formed through a side wall of the casing and the like.

The invention claimed is:

1. An air cleaner comprising:
   a body formed with an air suction hole defined on a side of the body, and allowing air to be introduced into the body therethrough;
   a metal casing into which an upper section of the body is inserted from below;
   a flow creation mechanism disposed inside the casing to create an air flow into and through the air cleaner;
   a filter disposed in the body between the air suction hole and the flow creation mechanism configured to purify air;
   a capacitive switch partially exposed outside the casing through a switch exposure hole defined through the casing; and
   a printed circuit board (PCB) disposed between one side wall of the upper section of the body and an inner wall of the casing,
   wherein the body comprises a thickened portion formed at a lower end of the upper section of the body.

2. The air cleaner according to claim 1, wherein the capacitive switch comprises a touch button exposed through the switch exposure hole and a conductive gasket disposed between the touch button and the PCB to electrically connect the touch button to the PCB.

3. The air cleaner according to claim 2, wherein a surface of the touch button contacting the conductive gasket is curved inward.

4. The air cleaner according to claim 2, wherein the touch button has a larger width than the conductive gasket.

5. The air cleaner according to claim 1, wherein a wall portion of the casing defining the switch exposure hole is rounded on an inner side thereof.

6. The air cleaner according to claim 1, further comprising a support fin protruding from the one side wall of the body and comprises a free end extending to contact an inner surface of the casing.

7. The air cleaner according to claim 1, wherein the body comprises a secured portion connected to the upper section, and an upper surface of the secured portion connected to the upper section extends from both side edges of the upper surface beyond the upper section to form a stepped portion.

8. The air cleaner according to claim 7, wherein, with the upper section inserted into the casing, a lower end of the casing contacts the stepped portion.

9. The air cleaner according to claim 1, wherein the body includes a lower section defined below the thickened portion.

10. The air cleaner according to claim 9, wherein the lower section of the body is configured to be exposed from the casing.

11. An air cleaner comprising:
a body formed with an air suction hole defined on a side of the body, and allowing air to be introduced into the body therethrough;
a metal casing into which an upper section of the body is inserted from below;
a flow creation mechanism disposed inside the casing to create an air flow into and through the air cleaner;
a filter disposed in the body between the air suction hole and the flow creation mechanism configured to purify air;
a capacitive switch partially exposed outside the casing through a switch exposure hole defined through the casing; and
a printed circuit board (PCB) disposed between one side wall of the upper section of the body and an inner wall of the casing,
wherein the capacitive switch comprises a touch button exposed through the switch exposure hole and a conductive gasket disposed between the touch button and the PCB to electrically connect the touch button to the PCB, and
wherein the conductive gasket comprises a cuboidal elastic foam member and a conductive tape wrapped around the cuboidal elastic foam member.

12. An air cleaner comprising:
a body formed with an air suction hole defined on a side of the body, and allowing air to be introduced into the body therethrough;
a metal casing into which an upper section of the body is inserted from below;
a flow creation mechanism disposed inside the casing to create an air flow into and through the air cleaner;
a filter disposed in the body between the air suction hole and the flow creation mechanism configured to purify air;
a capacitive switch partially exposed outside the casing through a switch exposure hole defined through the casing; and
a printed circuit board (PCB) disposed between one side wall of the upper section of the body and an inner wall of the casing,
wherein the body comprises a secured portion connected to the upper section, the secured portion comprising a rail member formed inside the secured portion.

13. The air cleaner according to claim 12, further comprising a guide portion formed on an upper side of the rail member to receive the filter.

14. The air cleaner according to claim 13, further comprising a UV module disposed above the filter configured to emit UV light toward the filter.

15. The air cleaner according to claim 14, wherein the filter is a photocatalytic filter.

16. The air cleaner according to claim 12, further comprising a cover detachably coupled to the secured portion.

17. The air cleaner according to claim 16, wherein the cover comprises a guide bar, the guide bar being fastened to the rail member to couple the cover to the secured portion.

18. The air cleaner according to claim 16, further comprising a light shielding member disposed inside the body adjacent to a junction between an upper end of the cover and a lower end of the casing.

* * * * *